US011642460B2

(12) United States Patent
Guerra et al.

(10) Patent No.: US 11,642,460 B2
(45) Date of Patent: *May 9, 2023

(54) MEDICATION TRACKING SYSTEM

(71) Applicant: CareFusion 303, Inc., San Diego, CA (US)

(72) Inventors: Jesse J. Guerra, San Diego, CA (US); Prabhu Chinnaiah, San Diego, CA (US); Richard Stor Wu, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/201,276

(22) Filed: Mar. 15, 2021

(65) Prior Publication Data
US 2021/0308374 A1    Oct. 7, 2021

Related U.S. Application Data

(63) Continuation of application No. 16/745,592, filed on Jan. 17, 2020, now Pat. No. 10,980,940.
(Continued)

(51) Int. Cl.
*G08B 1/08*     (2006.01)
*A61M 5/168*    (2006.01)
(Continued)

(52) U.S. Cl.
CPC ...... *A61M 5/1684* (2013.01); *A61M 5/31568* (2013.01); *H04W 4/14* (2013.01);
(Continued)

(58) Field of Classification Search
CPC ........... A61M 5/1684; A61M 5/31568; A61M 2205/18; A61M 2205/3389; A61M 2205/50; H04W 4/14; H04W 4/20
(Continued)

(56) References Cited

U.S. PATENT DOCUMENTS 5,945,651 A    8/1999  Chorosinski et al.
6,650,964 B2  11/2003  Spano, Jr. et al.
(Continued)

FOREIGN PATENT DOCUMENTS

AU    2017 279 693 A1    1/2018
CA        2 636 115 C    6/2014
(Continued)

OTHER PUBLICATIONS

Benjamin, X.C. et al. (2012). "Visual identification of medicine boxes using features matching." *IEEE International Conference on Virtual Environments Human-Computer Interfaces and Measurement Systems (VECIMS)* Proceedings, 43-47. Doi: 10.1109/VECIMS.2012.6273190.
(Continued)

*Primary Examiner* — Tai T Nguyen
(74) *Attorney, Agent, or Firm* — Mintz, Levin, Cohn, Ferris, Glovsky and Popeo, P.C.

(57)    ABSTRACT

A method may include receiving, from a volume meter at a pump configured to deliver medication to a patient, data indicative of a volume of a medication present in a syringe inserted in the pump. A first counter may be updated, based on the data, in response to the medication being delivered to the patient as a first dose type. A second counter may be updated, based on the data, in response to the medication being delivered to the patient as a second dose type. The volume of the medication delivered to the patient may be determined based on the first counter and/or the second counter. An electronic alert may be sent to a mobile device in response to one or more anomalies being present in the volume of the medication delivered to the patient. Related methods and articles of manufacture, including apparatuses and computer program products, are also disclosed.

20 Claims, 11 Drawing Sheets

Related U.S. Application Data

(60) Provisional application No. 62/794,306, filed on Jan. 18, 2019.

(51) Int. Cl.
   *A61M 5/315* (2006.01)
   *H04W 4/14* (2009.01)
   *H04W 4/20* (2018.01)

(52) U.S. Cl.
   CPC .......... *H04W 4/20* (2013.01); *A61M 2205/18* (2013.01); *A61M 2205/3389* (2013.01); *A61M 2205/50* (2013.01); *A61M 2205/52* (2013.01); *A61M 2205/6009* (2013.01); *A61M 2205/6054* (2013.01); *A61M 2205/6072* (2013.01)

(58) Field of Classification Search
   USPC ...................................................... 340/539.1
   See application file for complete search history.

(56) References Cited

U.S. PATENT DOCUMENTS

| | | | |
|---|---|---|---|
| 6,671,579 | B2 | 12/2003 | Spano, Jr. et al. |
| 6,842,736 | B1 | 1/2005 | Brzozowski |
| 6,868,344 | B1 | 3/2005 | Nelson |
| 7,119,689 | B2 | 10/2006 | Mallett et al. |
| 7,184,897 | B2 | 2/2007 | Nelson |
| 7,275,645 | B2 | 10/2007 | Mallett et al. |
| 7,303,081 | B2 | 12/2007 | Mallett et al. |
| 7,311,207 | B2 | 12/2007 | Mallett et al. |
| 7,318,529 | B2 | 1/2008 | Mallett et al. |
| 7,562,025 | B2 | 7/2009 | Mallett et al. |
| 8,147,479 | B1 * | 4/2012 | Wach ...................... G01F 1/661 604/522 |
| 8,195,328 | B2 | 6/2012 | Mallett et al. |
| 8,280,550 | B2 | 10/2012 | Levy et al. |
| 8,319,669 | B2 | 11/2012 | Weller |
| 8,357,114 | B2 | 1/2013 | Poutiatine et al. |
| 8,595,021 | B2 | 11/2013 | Mallett et al. |
| 8,606,596 | B1 | 12/2013 | Bochenko et al. |
| 8,725,532 | B1 | 5/2014 | Ringold |
| 8,738,177 | B2 | 5/2014 | van Ooyen et al. |
| 8,768,724 | B2 | 7/2014 | Whiddon et al. |
| 8,905,964 | B2 | 12/2014 | Poutiatine et al. |
| 9,158,892 | B2 | 10/2015 | Levy et al. |
| 9,202,052 | B1 | 12/2015 | Fang et al. |
| 9,227,025 | B2 | 1/2016 | Butterfield et al. |
| 9,354,178 | B2 | 5/2016 | Lee |
| 9,427,520 | B2 | 8/2016 | Batch et al. |
| 9,456,958 | B2 | 10/2016 | Reddy et al. |
| 9,523,635 | B2 | 12/2016 | Tilden |
| 9,636,273 | B1 | 5/2017 | Harris |
| 9,752,935 | B2 | 9/2017 | Marquardt et al. |
| 9,796,526 | B2 | 10/2017 | Smith et al. |
| 9,817,850 | B2 | 11/2017 | Dubbels et al. |
| 9,836,485 | B2 | 12/2017 | Dubbels et al. |
| 9,842,196 | B2 | 12/2017 | Utech et al. |
| 9,881,129 | B1 | 1/2018 | Cave |
| 9,958,324 | B1 | 5/2018 | Marquardt et al. |
| 10,032,344 | B2 | 7/2018 | Nelson et al. |
| 10,101,269 | B2 | 10/2018 | Judge et al. |
| 10,187,288 | B2 | 1/2019 | Parker et al. |
| 10,209,176 | B2 | 2/2019 | Proskurowski et al. |
| 10,241,038 | B2 | 3/2019 | Nishimura et al. |
| 10,249,153 | B2 | 4/2019 | Nelson et al. |
| 10,309,832 | B2 | 6/2019 | Marquardt et al. |
| 10,345,242 | B2 | 7/2019 | Zhao et al. |
| 10,832,207 | B2 | 11/2020 | Vahlberg et al. |
| 11,037,666 | B1 | 6/2021 | Benoit et al. |
| 11,116,892 | B2 * | 9/2021 | Brady ............... A61M 5/16813 |
| 11,147,914 | B2 * | 10/2021 | Estes .................. A61M 5/158 |
| 2003/0158751 | A1 | 8/2003 | Suresh et al. |
| 2008/0059226 | A1 | 3/2008 | Melker et al. |
| 2008/0082360 | A1 | 4/2008 | Bailey et al. |
| 2008/0140715 | A1 | 6/2008 | Hakos |
| 2008/0288430 | A1 | 11/2008 | Friedlander et al. |
| 2008/0306796 | A1 | 12/2008 | Zimmerman et al. |
| 2008/0319795 | A1 | 12/2008 | Poteet et al. |
| 2009/0160646 | A1 | 6/2009 | Mackenzie et al. |
| 2011/0016110 | A1 | 1/2011 | Egi et al. |
| 2011/0161108 | A1 | 6/2011 | Miller et al. |
| 2012/0226447 | A1 | 9/2012 | Nelson et al. |
| 2012/0265336 | A1 | 10/2012 | Mallett et al. |
| 2012/0325330 | A1 | 12/2012 | Prince et al. |
| 2013/0002429 | A1 | 1/2013 | Johnson |
| 2013/0018356 | A1 | 1/2013 | Prince et al. |
| 2013/0070090 | A1 | 3/2013 | Bufalini et al. |
| 2013/0144254 | A1 | 6/2013 | Amirouche et al. |
| 2013/0253700 | A1 | 9/2013 | Carson et al. |
| 2013/0282392 | A1 | 10/2013 | Wurm |
| 2013/0325727 | A1 | 12/2013 | MacDonell et al. |
| 2014/0074284 | A1 | 3/2014 | Czaplewski et al. |
| 2014/0149131 | A1 | 5/2014 | Bear et al. |
| 2014/0249776 | A1 | 9/2014 | King et al. |
| 2014/0277707 | A1 | 9/2014 | Akdogan et al. |
| 2014/0375324 | A1 | 12/2014 | Matsiev et al. |
| 2015/0038898 | A1 | 2/2015 | Palmer et al. |
| 2015/0081324 | A1 | 3/2015 | Adjaoute |
| 2015/0109437 | A1 | 4/2015 | Yang et al. |
| 2015/0272825 | A1 | 10/2015 | Lim et al. |
| 2015/0286783 | A1 | 10/2015 | Kumar et al. |
| 2015/0323369 | A1 | 11/2015 | Marquardt |
| 2015/0339456 | A1 | 11/2015 | Sprintz |
| 2015/0362350 | A1 | 12/2015 | Miller et al. |
| 2016/0034274 | A1 | 2/2016 | Diao et al. |
| 2016/0062371 | A1 | 3/2016 | Davidian et al. |
| 2016/0161705 | A1 | 6/2016 | Marquardt et al. |
| 2016/0166766 | A1 | 6/2016 | Schuster et al. |
| 2016/0283691 | A1 | 9/2016 | Ali |
| 2017/0017760 | A1 | 1/2017 | Freese et al. |
| 2017/0032102 | A1 | 2/2017 | Skoda |
| 2017/0076065 | A1 | 3/2017 | Darr et al. |
| 2017/0083681 | A1 | 3/2017 | Sprintz et al. |
| 2017/0103203 | A1 | 4/2017 | Sharma et al. |
| 2017/0108480 | A1 | 4/2017 | Clark et al. |
| 2017/0109480 | A1 | 4/2017 | Vahlberg |
| 2017/0109497 | A1 | 4/2017 | Tribble et al. |
| 2017/0120035 | A1 | 5/2017 | Butterfield et al. |
| 2018/0028408 | A1 | 2/2018 | Li et al. |
| 2018/0039736 | A1 | 2/2018 | Williams |
| 2018/0046651 | A1 | 2/2018 | Dubbels et al. |
| 2018/0157803 | A1 | 6/2018 | Mirov |
| 2018/0192942 | A1 | 7/2018 | Clark et al. |
| 2018/0231415 | A1 | 8/2018 | Marquardt et al. |
| 2018/0247703 | A1 | 8/2018 | D'Amato |
| 2018/0259446 | A1 | 9/2018 | Coffey et al. |
| 2018/0299375 | A1 | 10/2018 | Young et al. |
| 2018/0330824 | A1 | 11/2018 | Athey et al. |
| 2018/0365386 | A1 | 12/2018 | Vanderveen |
| 2019/0088354 | A1 | 3/2019 | Yanowitz et al. |
| 2019/0117883 | A1 | 4/2019 | Abrams et al. |
| 2019/0180862 | A1 | 6/2019 | Wisser et al. |
| 2019/0244699 | A1 | 8/2019 | Loebig et al. |
| 2019/0247703 | A1 | 8/2019 | Welde et al. |
| 2019/0341142 | A1 | 11/2019 | Nag et al. |
| 2019/0355461 | A1 | 11/2019 | Kumar et al. |
| 2020/0085686 | A1 | 3/2020 | Aliakbarian et al. |
| 2020/0098474 | A1 | 3/2020 | Vanderveen |
| 2020/0219611 | A1 | 7/2020 | Nag et al. |
| 2020/0222627 | A1 | 7/2020 | Guerra et al. |
| 2020/0230316 | A1 | 7/2020 | Guerra et al. |
| 2021/0133201 | A1 | 5/2021 | Tribble et al. |
| 2021/0308385 | A1 * | 10/2021 | Nisha ................ G16H 20/17 |
| 2022/0093239 | A1 | 3/2022 | Nag et al. |

FOREIGN PATENT DOCUMENTS

| | | |
|---|---|---|
| CA | 2 848 274 C | 9/2016 |
| EP | 1 973 593 B1 | 4/2013 |
| EP | 1 593 076 B1 | 10/2019 |
| WO | WO-2006/034367 A2 | 3/2006 |
| WO | WO-2014/055925 A1 | 4/2014 |

(56) References Cited

FOREIGN PATENT DOCUMENTS

| WO | WO-2015/187682 A1 | 12/2015 |
| WO | WO-2019/028004 A1 | 2/2019 |
| WO | WO-2019/031331 A1 | 2/2019 |

OTHER PUBLICATIONS

Cakaloglu, T. (Nov. 1, 2017). "Medi-Deep: Deep control in a medication usage." *2017 IEEE International Conference of Bioinfomratice and Biomedicine (BIBM)*, 899-904. Doi: 10.1109/BIBM.2017.8217776.

Neuman, M.R. et al. (May 13, 2012), "Advances in Medical Devices and Medical Electronics," in Proceedings of the IEEE, vol. 100, No. Special Centennial Issue, pp. 1537-1550,doi: 10.1109/JPROC.2012.2190684.

Qui et al. (2016) "A survey of machine learning for big data processing." *EURASIP Journal on Advances in Signal Processing*, Article No. 67, 16 pages.

Shishvan, O. Rajabi et al. (2018). "Machine Intelligence in Healthcare and Medical Cyber Physical Systems: A Survey." *IEEE Access*. vol. 6, 46419-46494. doi: 10.1109/ACCESS.2018.2866049.

Uniyal, D. et al. (Nov. 7, 2014), "Pervasive Healthcare—A Comprehensive Survey of Tools and Techniques," arXiv:1411.1821v1, 48 pages.

Yang, J., McAuley, J.J., & Leskovec, J. (2013). "Community Detection in Networks with Node Attributes." 2013 IEEE 13th International Conference on Data Mining, 1151-1156.

Yaniv, Z. et al. (Oct. 1, 2016). "The National Library of Medicine Pill Image Recognition Challenge: An Initial Report." *Oct. 2016 IEEE Applied Imagery Pattern Recognition Workshop, (AIPR)*, 1-9. Doi: 10.1109/AIPR.2016.8010584.

Zhan, A. et al. (Jan. 5, 2016) "High Frequency Remote Monitoring of Parkinson's Disease via Smartphone: Platform Overview and Medication Response Detection," Retrieved Apr. 29, 2021. 12 pages.

\* cited by examiner

Channel A - Morphine
Neonatal Care Area

CHANNEL A STATUS SUMMARY

| Start Time (Channel A) | ____ AM/PM |
| End Time (Channel A) | ____ AM/PM |
| Delivery Rate | ____ mL/hour |
| VTBI | ____ mL |
| Vol. Infused (Channel A) | ____ mL |
| Cumulative Volume | ____ mL |

> SELECT CUMULATIVE VOLUME TIME PERIOD

| 1 hour | 12 hours | 48 hours | Custom |

MEDICATION TRACKING SYSTEM

CROSS-REFERENCE TO RELATED APPLICATIONS

The present application is a continuation of U.S. application Ser. No. 16/745,592, now U.S. Pat. No. 10,980,940, filed on Jan. 17, 2020, and titled, "MEDICATION TRACKING SYSTEM," which claims priority to U.S. Provisional Application No. 62/794,306, filed on Jan. 18, 2019, and titled "MEDICATION TRACKING SYSTEM," the entirety of each of which is incorporated by reference herein.

TECHNICAL FIELD

The subject matter described herein relates generally to the dispensation of pharmaceuticals and more specifically to a tracking system for the delivery of medication.

BACKGROUND

Patient-controlled analgesia pumps may provide patients direct control over the delivery of some medications including, for example, opioid pain medications, which are otherwise administered in single doses by medical professionals via intramuscular injections or intravenous injections. A patient-controlled analgesia pump is a computerized pump that houses a reservoir containing multiple doses of a medication and is connected directly to a patient's vein. The patient-controlled analgesia pump may be configured to deliver a constant flow of the medication to the patient. Alternatively and/or additionally, the patient-controlled analgesia pump may allow the patient to self-administer individual doses of the medication on an as-needed basis.

SUMMARY

Systems, methods, and articles of manufacture, including computer program products, are provided for tracking medication delivered to a patient using a patient-controlled analgesic pump. For example, a patient-controlled analgesic pump may be communicatively coupled with a tracking engine configured to track the volume of a medication delivered to a patient over the administration of multiple doses and/or syringes of the medication.

According to some aspects, a method may include receiving, from a volume meter at a pump, a first data indicative of a volume of a first medication present in a first syringe inserted in the pump. The pump may deliver the first medication to a patient. The method may also include updating, based at least on the first data, a first counter in response to the first medication being delivered to the patient from the first syringe as a first dose type or a second counter in response to the first medication being delivered to the patient from the first syringe as a second dose type. The method may further include determining, based at least on the first counter and/or the second counter, a first volume of the first medication delivered to the patient. The method may also include sending, to a mobile device, an electronic alert in response to one or more anomalies being present in the first volume of the first medication delivered to the patient.

In some aspects, the first volume includes a first individual volume of the first medication that is delivered to the patient as the first dose type, a second individual volume of the first medication that is delivered to the patient as the second dose type, and/or a total volume of the first medication that is delivered to the patient as the first dose type and the second dose type.

In some aspects, the method may also include receiving, from a tag reader at the pump, a second data identifying a second medication in a second syringe that is inserted into the pump to replace the first syringe. The method may also include resetting the first counter and the second counter in response to the second medication being a different medication than the first medication included in the first syringe.

In some aspects, the method may also include updating the first counter in response to the second medication being delivered to the patient as the first dose type and/or the second counter in response to the second medication being delivered to the patient as the second dose type.

In some aspects, the method may also include in response to the second medication being a same medication as the first medication, updating the first counter in response to the first medication being delivered to the patient from the second syringe as the first dose type and/or the second counter in response to the first medication being delivered to the patient from the second syringe as the second dose type.

In some aspects, the method may also include in response to the second data indicating that the second syringe is associated with a different patient than the first syringe, resetting the first counter and the second counter.

In some aspects, the tag reader may read a first identifier tag associated with the first syringe and/or a second identifier tag associated with the second syringe. The first identifier tag and/or the second identifier tag may include a barcode, a quick response (QR) code, and/or a radio frequency identification (RFID) tag.

In some aspects, the first dose type and the second dose type include a different one of a patient demand dose, a clinician dose, a loading dose, and a maintenance dose.

In some aspects, the one or more anomalies include the first volume being greater than a maximum threshold value or less than a minimum threshold value.

Implementations of the current subject matter can include, but are not limited to, methods consistent with the descriptions provided herein as well as articles that comprise a tangibly embodied machine-readable medium operable to cause one or more machines (e.g., computers, etc.) to result in operations implementing one or more of the described features. Similarly, computer systems are also described that may include one or more processors and one or more memories coupled to the one or more processors. A memory, which can include a non-transitory computer-readable or machine-readable storage medium, may include, encode, store, or the like one or more programs that cause one or more processors to perform one or more of the operations described herein. Computer implemented methods consistent with one or more implementations of the current subject matter can be implemented by one or more data processors residing in a single computing system or multiple computing systems. Such multiple computing systems can be connected and can exchange data and/or commands or other instructions or the like via one or more connections, including, for example, to a connection over a network (e.g. the Internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to the tracking of medication delivered to a patient, it should be readily understood that such features are not intended to be limiting. The claims that follow this disclosure are intended to define the scope of the protected subject matter.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

FIG. 4 depicts an example user interface, in accordance with some example embodiments;

When practical, similar reference numbers denote similar structures, features, or elements.

DETAILED DESCRIPTION

A patient-controlled analgesic pump may allow a patient to directly control the delivery of a medication instead of having to rely on medical professionals to administer the opioid pain medication via intramuscular injections or intravenous injections. For example, the patient-controlled analgesic pump may include a syringe containing multiple doses of the medication, which may be administered to a patient as one or more patient demand doses, clinician doses, loading doses, and/or maintenance doses. Moreover, the patient may receive multiple syringes of the medication during the course of treatment. Consequently, the actual volume of medication that is delivered to the patient may be difficult to track, thereby giving rise to opportunities for medication to be abused or diverted to third parties who are not legally authorized to receive, possess, and/or consume the medication. As such, in some example embodiments, a tracking engine may be configured to determine the actual volume of medication delivered to a patient across multiple doses and/or syringes of the medication administered to the patient. Tracking the actual volume of medication delivered to the patient may reduce and/or eliminate opportunities for abuse or diversion.

Figure 1A:
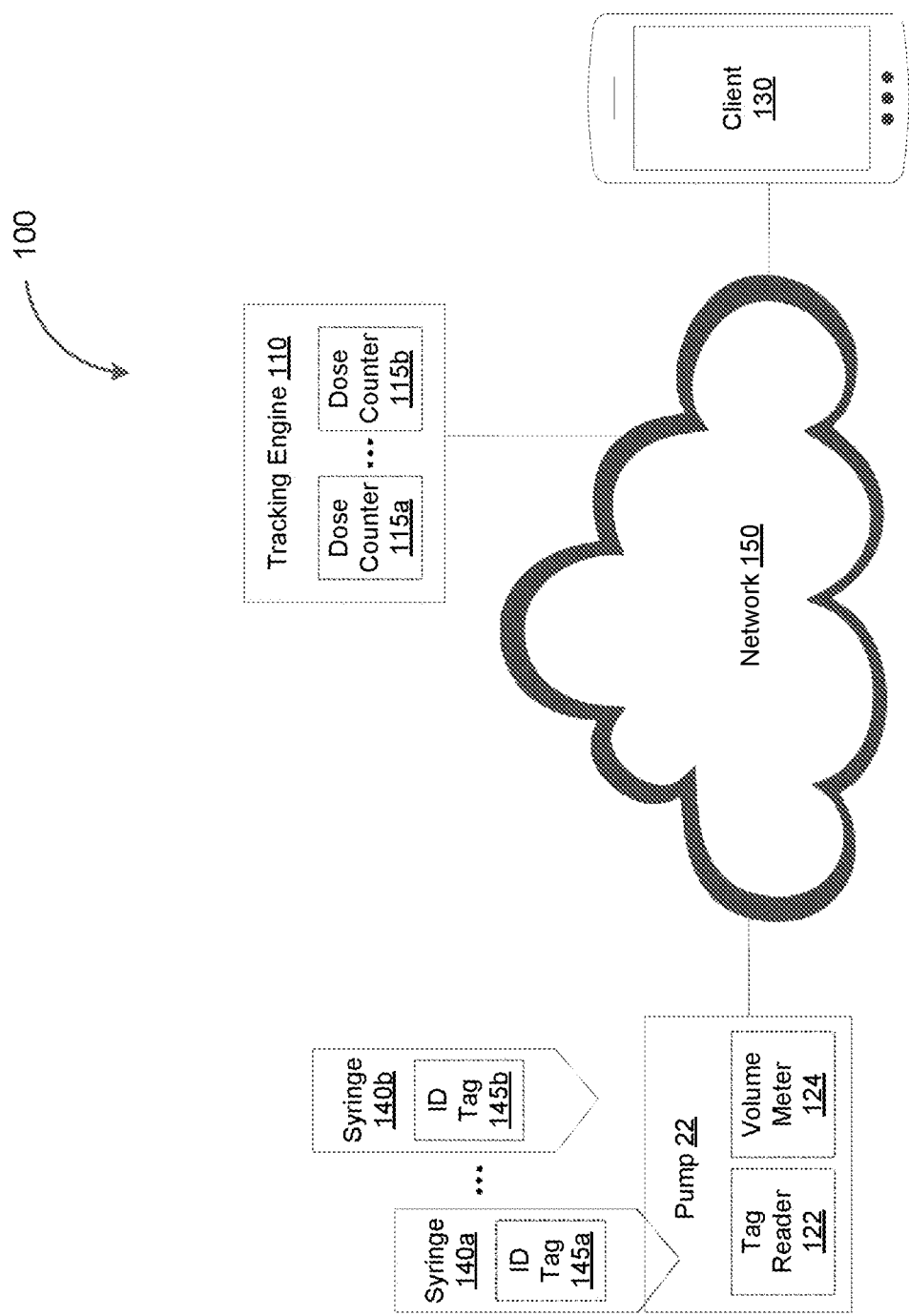
FIG. 1A depicts a system diagram illustrating a medication tracking system, in accordance with some example embodiments.

FIG. 1A depicts a system diagram illustrating a medication tracking system 100, in accordance with some example embodiments. Referring to FIG. 1A, the medication tracking system 100 may include a tracking engine 110, a pump 22, and a client 130. As FIG. 1A shows, the tracking engine 110, the pump 22, and/or the client 130 may be communicatively coupled via a network 150. The client 130 may be a mobile device such as, for example, a smartphone, a tablet computer, a wearable apparatus, and/or the like. However, it should be appreciated that the client 130 may be any processor-based device including, for example, a desktop computer, a laptop computer, a workstation, and/or the like. Meanwhile, the network 150 may be any wired and/or wireless network including, for example, a public land mobile network (PLMN), a local area network (LAN), a virtual local area network (VLAN), a wide area network (WAN), the Internet, and/or the like. Additionally and/or alternatively, the tracking engine 110 and/or the client 130 may form at least a part of the pump 22.

The pump 22 may be a patient-controlled analgesic (PCA) pump configured to deliver a medication to a patient. However, it should be appreciated that the pump 22 may be any infusion system configured to deliver a substance (e.g., fluid, nutrients, medication, and/or the like) to a patient's circulatory system or epidural space via, for example, intravenous infusion, subcutaneous infusion, arterial infusion, epidural infusion, and/or the like. Alternatively, the pump 22 may be an infusion system configured to deliver a substance (e.g., fluid, nutrients, medication, and/or the like) to a patient's digestive system via a nasogastric tube (NG), a percutaneous endoscopic gastrostomy tube (PEG), nasojejunal tube (NJ), and/or the like. Moreover, the pump 22 may be part of a patient care system that includes one or more additional pumps.

As FIG. 1A shows, the pump 22 may be configured to receive one or more syringes containing a medication such as, for example, a opioid pain medication (e.g., morphine, hydromorphone, fentanyl, and/or the like). For example, a first syringe 140a containing a first medication may be inserted into the pump 22 such that the pump 22 may deliver the first medication to the patient in one or more doses including, for example, patient demand doses, clinician doses, loading doses, and/or maintenance doses. The first syringe 140a may be removed from the pump 22 and replaced with a second syringe 140b containing the first medication or a second medication, for example, when a threshold quantity of the first medication remains in the first syringe 140a, when a threshold quantity of the first medication has been delivered to the patient from the first syringe 140a, and/or the like.

Figure 2A:
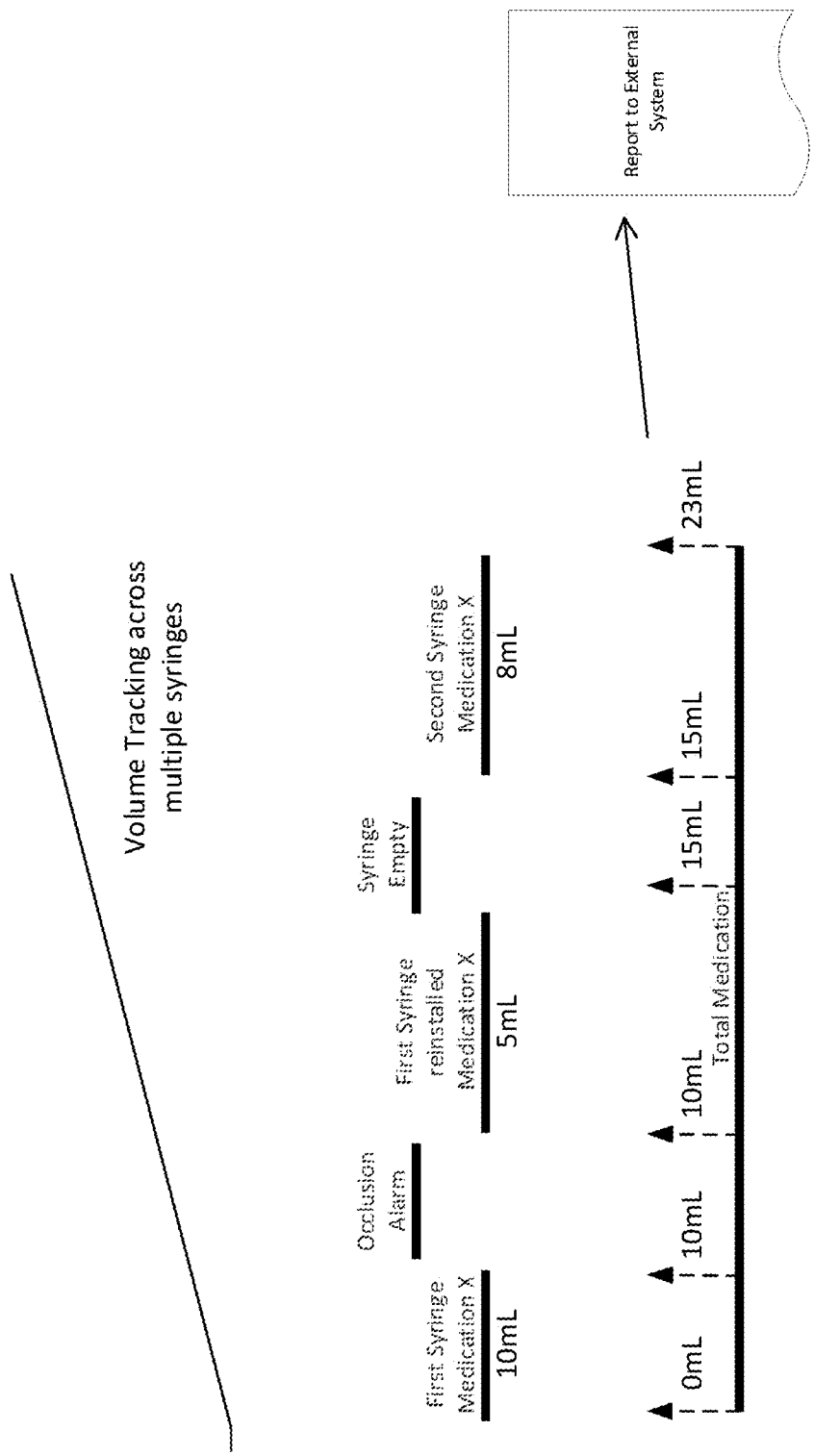
FIG. 2A depicts volume tracking across multiple syringes of a medication administered to a patient, in accordance with some example embodiments.

In some example embodiments, the tracking engine 110 may be configured to determine the volume of one or more medications delivered to a patient via the pump 22 across multiple syringes of the medication including, for example, the first syringe 140a, the second syringe 140b, and/or the like. For example, the tracking engine 110 may track the volume of the first medication delivered to the patient in response to the first syringe 140a being inserted into the pump 22 and/or the first medication from the first syringe 140a being delivered to the patient. Alternatively and/or additionally, the tracking engine 110 may track the volume of the second medication delivered to the patient in response to the second syringe 140b being inserted into the pump 22 and/or the second medication from the second syringe 140b being delivered to the patient. To further illustrate, FIG. 2A depicts volume tracking across multiple syringes of the same medication administered to the patient, in accordance with some example embodiments. For example, the tracking engine 110 may track a volume of a medication delivered by a first syringe (e.g., the first syringe 140a) and a second syringe (e.g., the second syringe 140b) after the medication from the first syringe has been delivered to the patient. As described in more detail below, the tracking engine 110 may report the tracked volume of medication delivered by each syringe to a device, such as a display having a user interface of the client 130 and/or the pump 22 (see FIG. 4).

Figure 2B:
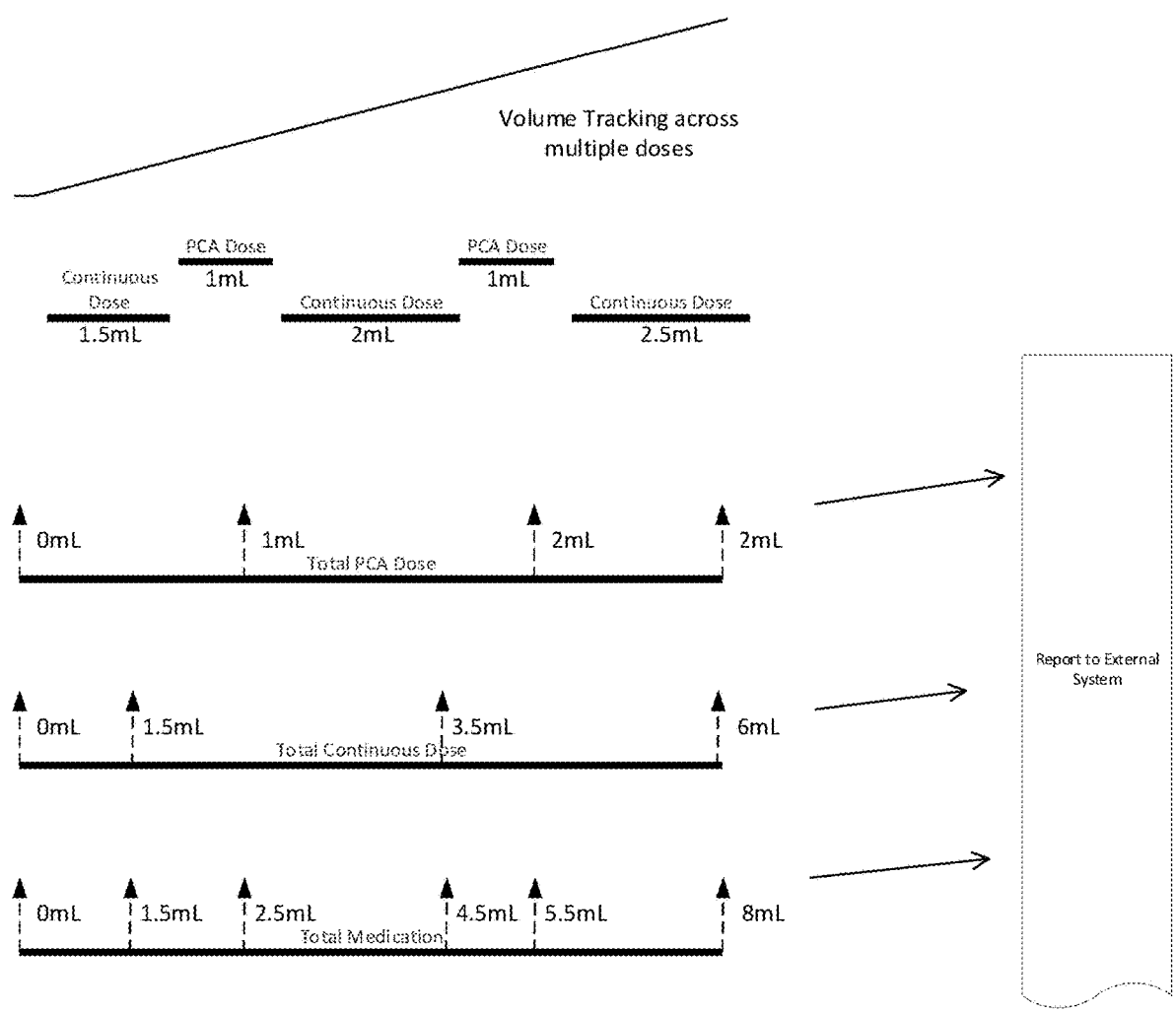
FIG. 2B depicts volume tracking over multiple doses of a medication administered to a patient, in accordance with some example embodiments.

Furthermore, the tracking engine 110 may track the volume of the one or more medications that is delivered to the patient from the first syringe 140a and/or the second syringe 140b as different doses of medication. For instances, the tracking engine 110 may track the doses of the first medication and/or the second medication that are delivered to the patient as patient demand doses, clinician doses, loading doses, maintenance doses, and/or the like. To further illustrate, FIG. 2B depicts volume tracking over multiple doses of the same medication administered to a patient, in accordance with some example embodiments. As described in more detail below, the tracking engine 110 may report the tracked volume of medication delivered by each syringe, corresponding to each type of dose, to a device, such as a display having a user interface of the client 130 and/or the pump 22 (see FIG. 4).

As used herein, a patient demand dose may refer to a single dose of the medication that the pump 22 delivers to the patient in response to a request from the patient while a clinician dose may refer to a single dose of the medication that the pump 22 delivers to the patient in response to a request from a medical professional. Meanwhile, a loading dose may refer a higher dose of the medication that the pump 22 delivers to the patient at a start of a treatment whereas a maintenance dose may refer to a lower dose of the medication that the pump 22 delivers to the patient subsequent to one or more loading doses. Maintenance doses of the medication may be delivered to the patient, for example, in fixed size portions and/or at a set rate.

In some example embodiments, the tracking engine 110 may respond to a syringe of medication being inserted into the pump by at least identifying the medication contained in the syringe. For example, the tracking engine 110 may respond to the first syringe 140a being inserted into the pump 22 by at least identifying the medication that is contained in the first syringe 140a. Alternatively and/or additionally, the tracking engine 110 may respond to the second syringe 140b being inserted into the pump 22, for example, to replace the first syringe 140a, by at least identifying the medication contained in the second syringe 140b. If the tracking engine 110 determines that the second syringe 140b contains the same first medication as the first syringe 140a, the tracking engine 110 may continue to track the volume of the first medication that is being delivered to the patient from the second syringe 140b. By contrast, if the tracking engine 110 determines that the second syringe 140b contains the second medication instead of the first medication contained in the first syringe 140a, the tracking engine 110 may begin tracking the volume of the second medication that is being delivered to the patient from the second syringe 140b.

As FIG. 1A shows, the pump 22 may include a tag reader 122 configured to read a first identifier tag 145a associated with the first syringe 140a and/or a second identifier tag 145b associated with the second syringe 140b. For example, the first identifier tag 145a and/or the second identifier tag 145b may be a barcode, a quick response (QR) code, a radio frequency identification (RFID) tag, and/or the like. In some example embodiments, the first identifier tag 145a and/or the second identifier tag 145b may store data identifying the medication contained in the first syringe 140a and/or the second syringe 140b. Alternatively and/or additionally, the first identifier tag 145a and/or the second identifier tag 145b may store data identifying the patient, the medical professional, the compounding facility, and/or the treatment facility associated with the first syringe 140a and/or the second syringe 140b. Accordingly, the tracking engine 110 may identify, based on an output from the tag reader 122 at the pump 22, the medication, the patient, the medical professional, the compounding facility, and/or the treatment facility associated with each of the first syringe 140a and/or the second syringe 140b.

In some example embodiments, the tracking engine 110 may maintain one or more counters in order to track the volume of a medication delivered to the patient across multiple doses including, for example, patient demand doses, clinician doses, loading doses, and/or maintenance doses. Referring again to FIG. 1A, the tracking engine 110 may maintain a plurality of counters, each of which being configured to track the volume of a medication that is delivered to a patient as a corresponding dosage type. For instance, the tracking engine 110 may maintain a first dose counter 115a configured to track the volume of the medication delivered as one or more maintenance doses and a second dose counter 115b configured to track the volume of the medication delivered as one or more patient demand doses. The tracking engine 110 may update the first dose counter 115a and/or the second dose counter 115b based on an output from a volumetric device such as a volume meter 124 at or communicatively coupled with the pump 22.

The volume meter 124 may be configured to report, to the tracking engine 110, a volume of medication in the first syringe 140a and/or the second syringe 140b in response to one or more events including, for example, the insertion of a syringe, the administration of one or more doses of medication, and/or the like. The first dose counter 115a and/or the second dose counter 115b may be updated based at least on the volume of medication delivered from the first syringe 140a and/or the second syringe 140b reported by the volume meter 124. For instance, the volume meter 124 may report, to the tracking engine 110, an initial volume of the medication present in the first syringe 140a and/or the second syringe 140b when the first syringe 140a and/or the second syringe 140b is first inserted into the pump 22. Alternatively and/or additionally, the volume meter 124 may report, to the tracking engine 110, the volume of medication delivered from the first syringe 140a and/or the second syringe 140b after the administration of each dose of the medication. For example, the volume meter 124 may report, to the tracking engine 110, the volume of medication delivered by the first syringe 140a and/or the second syringe 140b after the administration of a patient demand dose, a clinician dose, a loading dose, and/or a maintenance dose. To determine an initial volume in a syringe, the volume meter 124 may receive programming information for the infusion such as a total volume to be infused. In some implementations, the volume meter 124 may use images to detect an identifier on the syringe or a level of medication within the syringe. Based on analysis of one or more images, the volume may be determined. The analysis may include identifying a fluid level within the syringe, identifying a marking on the syringe (e.g., volumetric graduation markings, structural references, scannable codes), or other detectable features. For example, if a fluid line may be identified at a particular volume marking thereby providing a volume within the syringe. As another example, the image may show information identifying the syringe such as a barcode or serial number. This information may be used to query a database to identify the volume of medication included by the preparer of the syringe (e.g., pharmacy, prescribing physician). In some implementations, the information may identify the geometry of the syringe which may then be used to generate a volume for the syringe.

The volume meter 124 may track specific volume of medication delivered. In some implementations, the volume meter 124 may provide an estimated volume delivered. The estimate may generated based at least in part on one or more of a flow rate, volume to be infused ("VTBI"), and duration of the infusion.

As noted, the tracking engine 110 may determine, based at least on a value of one or more counters maintained by the tracking engine 110, the volume of the first medication and/or the second medication delivered to the patient via the pump 22. For example, the tracking engine 110 may maintain the first dose counter 115*a* and/or the second dose counter 115*b* by at least storing a current value of the first dose counter 115*a* and/or the second dose counter 115*b*. Furthermore, the tracking engine 110 may update the current value of the first dose counter 115*a* and/or the second dose counter 115*b* to reflect the volume of a medication delivered to the patient as one or more maintenance doses and/or patient demand doses from the first syringe 140*a*, which contains the first medication. For example, the tracking engine 110 may increment the current value of the first dose counter 115 and/or the second dose counter 115*b* when one or more maintenance doses and/or patient demand doses are delivered to the patient from the first syringe 140*a*.

In some example embodiments, the tracking engine 110 may reset the first dose counter 115*a* and/or the second dose counter 115*b* when the first syringe 140*a* containing the first medication is replaced with the second syringe 140*b* containing the second medication. For instance, when the tracking engine 110 determines that the second syringe 140*b* contains the second medication instead of the first medication contained in the first syringe 140*a*, the tracking engine 110 may reset the first dose counter 115*a* and the second dose counter 115*b* by at least setting the current value of the first dose counter 115*a* and the second dose counter 115*b* to zero. The first dose counter 115*a* and the second dose counter 115*b* may be reset in order to avoid conflating the volume of the first medication that is delivered to the patient from the first syringe 140*a* with the volume of the second medication that is delivered to the patient from the second syringe 140*b*.

Alternatively and/or additionally, the tracking engine 110 may reset the first dose counter 115*a* and/or the second dose counter 115*b* in response to the patient being disassociated with the pump 22 and/or a different patient being associated with the pump 22. For example, the tracking engine 110 may set the current value of the first dose counter 115 and the second dose counter 115*b* to zero when the tracking engine 110 determines that the patient is disassociated with the pump 22 and/or a different patient is associated with the pump 22. The first dose counter 115*a* and the second dose counter 115*b* may be reset in this case in order to avoid conflating the volume of medication delivered to different patients.

In some example embodiments, the tracking engine 110 may be configured to generate one or more electronic alerts based on the volume of medication delivered to the patient across multiple doses and/or syringes. For example, the tracking engine 110 may generate the one or more electronic alerts in response to the volume of medication delivered to the patient being greater and/or less than a threshold value. The one or more electronic alerts may include wireless alert messages such as, for example, push notifications, short messaging service (SMS) message, and/or the like. Furthermore, the one or more electronic alerts may include an indication of the type of anomaly including, for example, the volume of medication delivered being greater than a threshold value, the volume of medication delivered being less than a threshold value, and/or the like. Alternatively and/or additionally, the one or more electronic alerts may include a patient identifier, a medication identifier, and/or a quantity of medication delivered to the patient. For instance, the one or more electronic alerts may specify the volume of medication, the quantity of doses, and/or the type of doses (e.g., patient demand doses, clinician doses, loading doses, maintenance doses, and/or the like) delivered to the patient.

Figure 3:
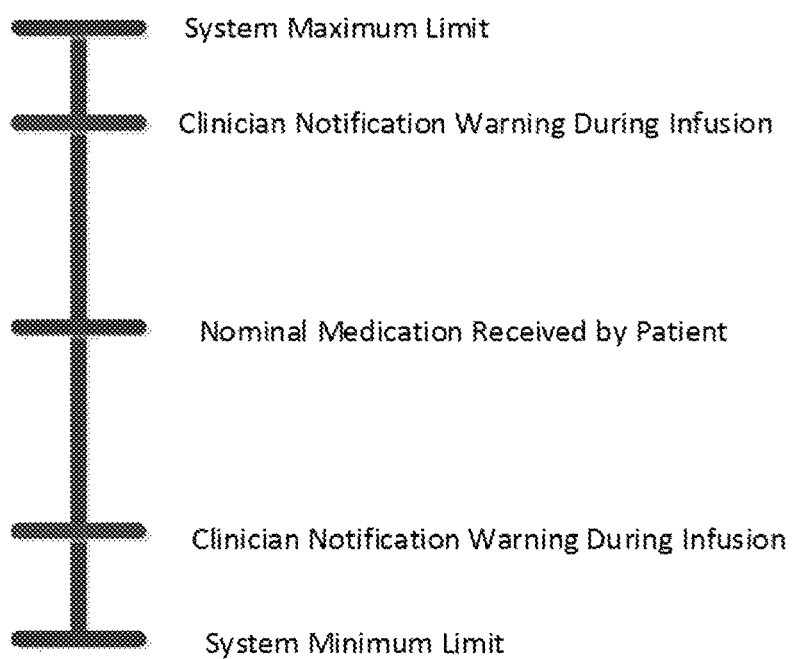
FIG. 3 depicts examples of alert thresholds associated with a medication tracking system, in accordance with some example embodiments.

For example, the tracking engine 110 may detect the presence of one or more anomalies in the volume of a medication delivered to the patient from the first syringe 140*a* and/or the second syringe 140*b*. Alternatively and/or additionally, the tracking engine 110 may detect the presence of one or more anomalies in the volume of the medication delivered to the patient as one or more patient demand doses, clinician doses, loading doses, and/or maintenance doses. The one or more anomalies may include the volume of medication delivered to the patient being greater and/or less than one or more threshold values. FIG. 3 depicts examples of alert thresholds associated with the medication tracking system 100, in accordance with some example embodiments. In response to detecting the presence of the one or more anomalies, the tracking engine 110 may generate the one or more alerts, which may be sent to a medical professional associated with the client 130.

Figure 1B:
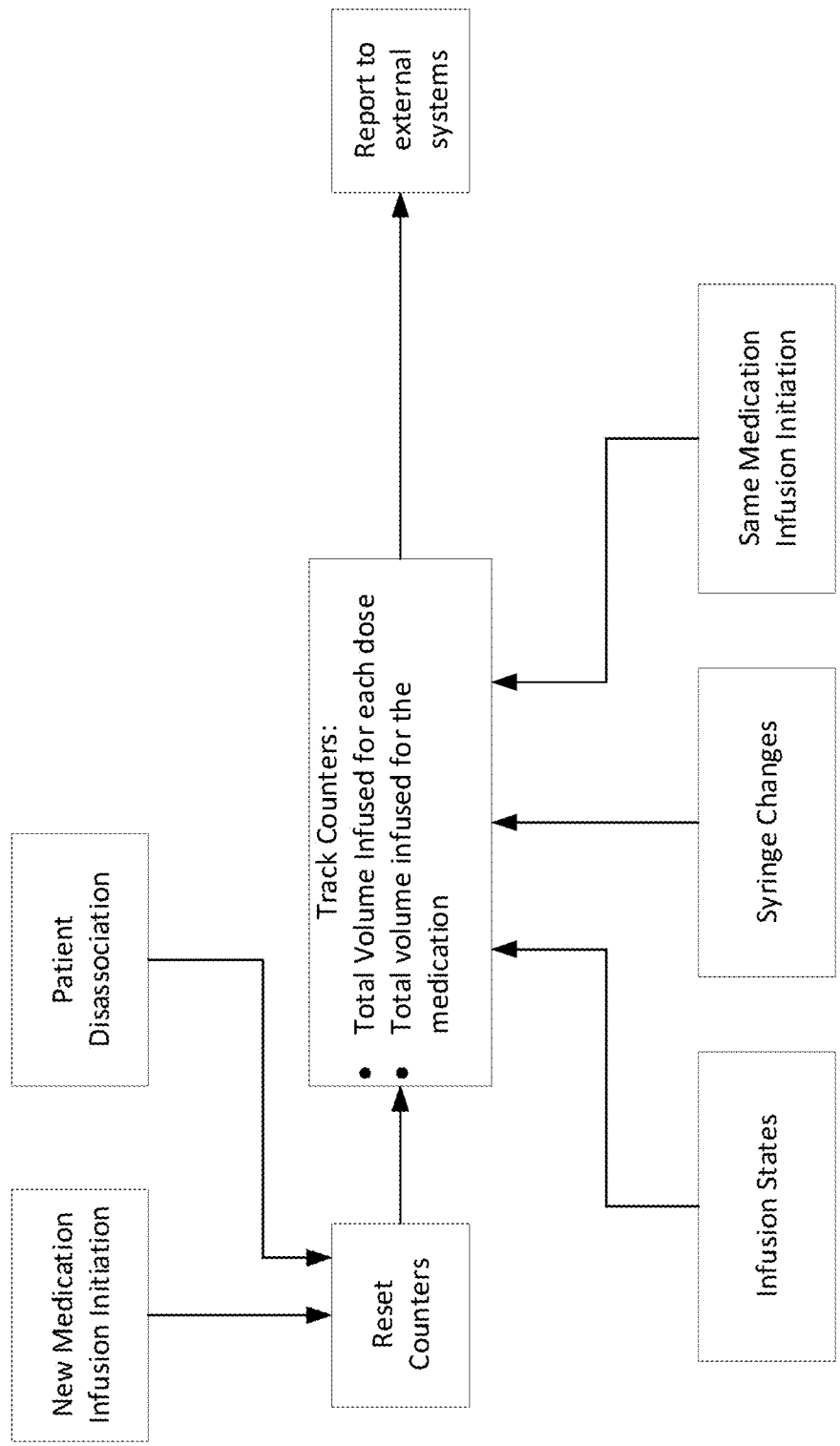
FIG. 1B depicts a block diagram illustrating a medication tracking system, in accordance with some example embodiments.

FIG. 1B depicts a block diagram illustrating the medication tracking system 100, in accordance with some example embodiments. Referring to FIGS. 1A-B, the tracking engine 110 of the medication tracking system 100 may be configured to maintain one or more counters including, for example, the first dose counter 115*a*, the second dose counter 115*b*, and/or the like. The value of the first dose counter 115*a* and/or the second dose counter 115*b* may be updated by the tracking engine 110 in response to the medication from the first syringe 140*a* being administered to the patient as one or more patient demand doses, clinician doses, loading doses, and/or maintenance doses. The tracking engine 110 may continue to update (e.g., increment) the first dose counter 115*a* and/or the second dose counter 115*b* when the first syringe 140*a* is replaced with the second syringe 140*b* if the tracking engine 110 determines, based at least on the first identifier tag 145*a* and/or the second identifier tag 145*b* read by the tag reader 122 at the pump 22, that the second syringe 140*b* is associated with at least the same medication and patient as the first syringe 140*a*.

Alternatively and/or additionally, FIG. 1B shows that the tracking engine 110 may be configured to reset the first dose counter 115*a* and the second dose counter 115*b* to a specified starting value if the tracking engine 110 determines, based at least on the first identifier tag 145*a* and/or the second identifier tag 145*b* read by the tag reader 122 at the pump 22, that the second syringe 140*b* is associated with a different medication and/or patient as the first syringe 140*a*. For example, if the tracking engine 110 determines that the second syringe 140b contains a different medication than the first syringe 140a, the first dose counter 115a and the second dose counter 115b may be reset in order to avoid conflating the volume of different medications delivered to the patient. Alternatively and/or additionally, if the tracking engine 110 determines that the second syringe 140b is associated with a different patient than the first syringe 140a, the first dose counter 115 and the second dose counter 115b may be reset in order to avoid conflating the volume of medication delivered to different patients.

Furthermore, FIG. 1B shows that the tracking engine 110 may be configured to generate one or more alerts, which may be sent to a medical professional associated with the client 130. The tracking engine 110 may generate the one or more alerts in response to the tracking engine 110 detecting the presence of one or more anomalies in the volume of a medication delivered to the patient, for example, from the first syringe 140a and/or the second syringe 140b. As FIG. 3 further illustrates, the tracking engine 110 may generate the one or more alerts in response to anomalies that include the volume of medication delivered to the patient being greater than a maximum threshold value and/or less than a minimum threshold value. The maximum threshold value and/or the minimum threshold value may be associated with a time interval such that the tracking engine 110 may generate the one or more alerts if an excessive volume and/or an inadequate volume of medication is delivered to the patient over the time interval (e.g., 24 hours and/or the like). For example, as shown in FIG. 2A, the tracking engine 110 may generate the one or more alerts, such as an occlusion alarm, if an inadequate volume of medication is delivered to the patient over a set time interval. In some embodiments, the volume of delivered medication is inadequate when a volume of the delivered medication is less than a volume of a desired dose of the medication and/or a volume of a syringe (e.g., the first syringe 140a and/or the second syringe 140b).

FIG. 4 depicts an example display including a user interface 300. The user interface 300 may form a part of the client 130 and/or the pump 22. The user interface 300 shows an example status summary of various aspects of the delivery of medication via a first pump channel (e.g., Channel A), which represents pump 22.

The user interface 300 may receive and display data received from the tracking engine 110 and/or flow meter 124. For example, the user interface 300 may display a start time of medication delivery by each syringe (e.g., the first syringe 140a, the second syringe 140b, etc.) coupled with the pump 22, an end time of medication delivery by each syringe coupled with the pump 22, an average, current, and/or desired delivery rate of medication delivered to the patient, the VTBI, a volume of medication already infused to the patient by the coupled syringe, and a cumulative volume of medication delivered to the patient. As noted above, the cumulative volume may be generated, at least in part, based on one or more of a flow rate, the VTBI, a duration of the infusion, a value of one or more counters maintained by the tracking engine 110, the volume of the first medication and/or the second medication delivered to the patient via the pump 22 and/or the like. The user interface 300 may allow for and/or receive a selection of one or more time periods, such as 1 hour, 12 hours, 48 hours, and/or other time intervals therebetween, of the cumulative volume.

Determining and displaying the cumulative volume over various time periods may help to ensure that the proper amount of medication has been delivered to the patient, help to limit or prevent diversion of the medication, and/or may assist users when converting patients to another form of treatment, such as a tapering plan, a pill, and/or the like. For example, the user interface 300 may provide the user with information about the start time and end time of medication delivery from a particular syringe, and the time at which a syringe is replaced. The user interface 300 may also display the cumulative volume of the medication delivered and the amount of medication left to be delivered to the patient. Thus, via the user display 300, the user may easily determine whether a volume of medication has been improperly diverted from the pump 22. Additionally and/or alternatively, based on the determined and/or displayed cumulative volume, a user may change the current treatment plan and/or taper the patient off of the medication being delivered to the patient.

Figure 5:
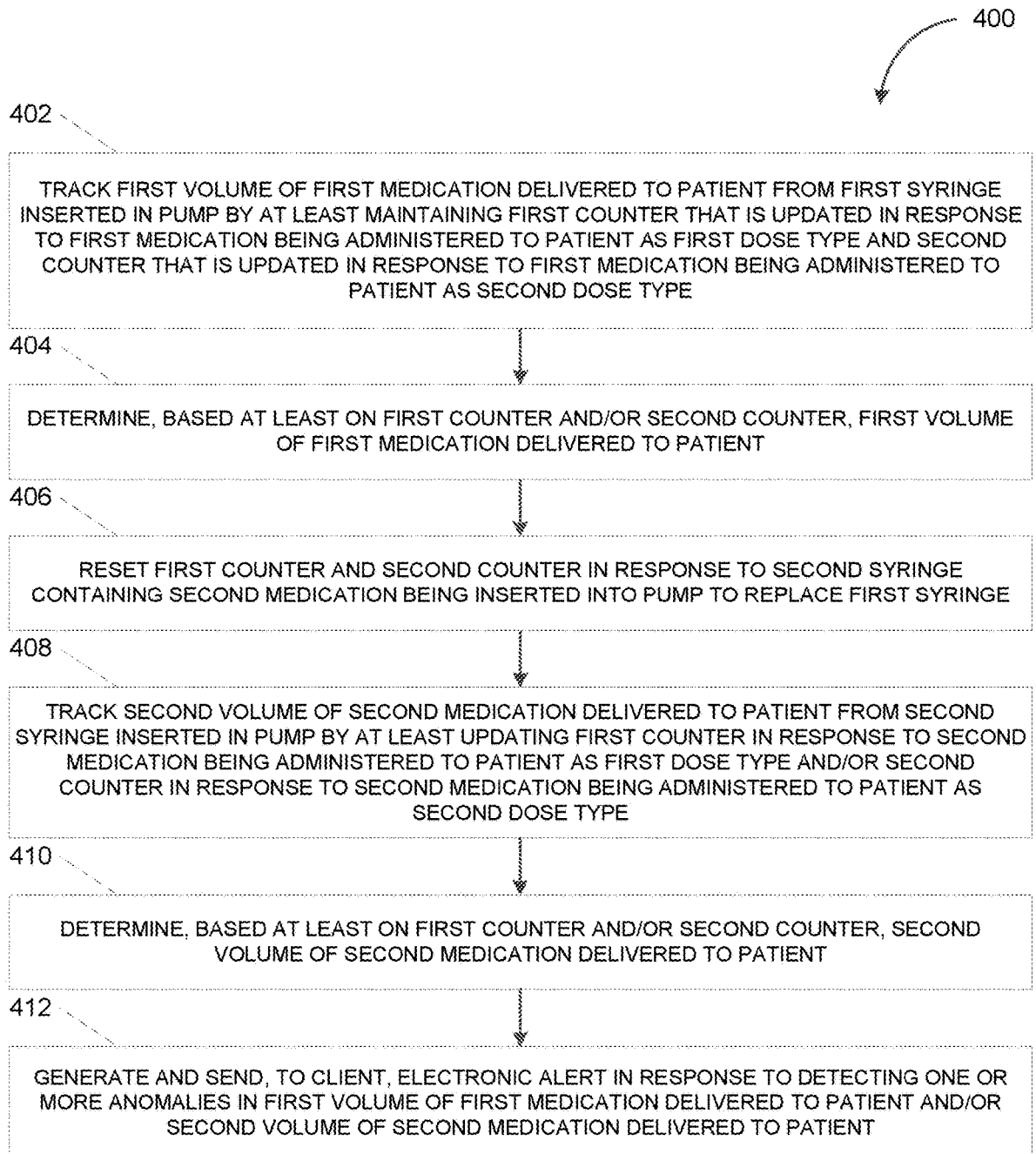
FIG. 5 depicts a flowchart illustrating a process for tracking the volume of a medication delivered to a patient, in accordance with some example embodiments.

FIG. 5 depicts a flowchart illustrating a process 400 for tracking the volume of a medication delivered to a patient, in accordance with some example embodiments. Referring to FIG. 5, the process 400 may be performed by the medication tracking system 100.

At 402, the medication tracking system 100 may track a first volume of a first medication delivered to a patient from a first syringe inserted in the pump 22 by at least maintaining a first counter that is updated in response to the first medication being administered to the patient as a first dose type and a second counter that is updated in response to the first medication being administered to the patient as a second dose type. For example, the tracking engine 110 may track the volume of the first medication delivered to the patient from the first syringe 140a in the pump 22 by at least maintaining one or more counters including, for example, the first dose counter 115a, the second dose counter 115b, and/or the like. Each of the counters may be associated with a dose type that may be administered to the patient including, for example, a patient demand dose, a clinician dose, a loading dose, and/or a maintenance dose. As such, the value of each of the counters may be updated in response to the medication in the first syringe 140a being delivered to the patient as a corresponding dose type. For instance, the first dose counter 115a may be updated whenever a maintenance dose of the first medication is administered to the patient from the first syringe 140a while the second dose counter 115b may be updated whenever a patient demand dose of the first medication is administered to the patient from the first syringe 140a.

At 404, the medication tracking system 100 may determine, based at least on the first counter and/or the second counter, the first volume of the first medication delivered to the patient. For example, the tracking engine 110 may determine, based at least on the respective values of the first dose counter 115a and the second dose counter 115b, the volume of the first medication that is administered to the patient as maintenance doses, the volume of the first medication that is administered to the patient as patient demand doses, and/or the total volume of the first medication that is administered to the patient across all dose types.

At 406, the medication tracking system 100 may reset the first counter and the second counter in response to a second syringe containing a second medication being inserted into the pump 22 to replace the first syringe. For example, the tracking engine 110 may reset the first dose counter 115a and the second dose counter 115b when the second syringe 140b that is inserted into the pump 22 to replace the first syringe 140a contains a different medication than the first syringe 140a. Alternatively and/or additionally, the first dose counter 115a and the second dose counter 115b may also be reset if the second syringe 140b is associated with a different patient with the first syringe 140a. In the event that the second syringe 140b contains the same medication and is associated with the same patient as the first syringe 140a, the tracking engine 110 may continue updating the first dose counter 115a and/or the second dose counter 115b without resetting the first dose counter 115a and/or the second dose counter 115b. The first dose counter 115a may be updated in response to the first medication being administered to the patient from the second syringe 140b as a maintenance dose while the second dose counter 115b may be updated in response to the first medication being administered to the patient from the second syringe 140b as a patient demand dose.

At 408, the medication tracking system 100 may track a second volume of the second medication delivered to a patient from the second syringe inserted in the pump 22 by at least updating the first counter in response to the second medication being administered to the patient as the first dose type and/or the second counter in response to the second medication being administered to the patient as the second dose type. For example, the tracking engine 110 may begin tracking the volume of the second medication delivered to the patient from the second syringe 140b when the second syringe 140b containing the second medication is inserted into the pump 22. The tracking engine 110 may track the volume of the second medication delivered to the patient by at least updating the first dose counter 115a whenever a maintenance dose of the second medication is administered to the patient from the second syringe 140b and the second dose counter 115b whenever a patient demand dose of the second medication is administered to the patient from the second syringe 140b.

At 410, the medication tracking system 100 may determine, based at least on the first counter and/or the second counter, the second volume of the second medication delivered to the patient. For example, the tracking engine 110 may determine, based at least on the respective values of the first dose counter 115a and the second dose counter 115b, the volume of the second medication that is administered to the patient as maintenance doses, the volume of the first medication that is administered to the patient as patient demand doses, and/or the total volume of the first medication that is administered to the patient across all dose types.

At 412, the medication tracking system 100 may generate and send, to the client 130, an electronic alert in response to detecting one or more anomalies in the first volume of the first medication delivered to the patient and/or the second volume of the second medication delivered to the patient. For example, the tracking engine 110 may detect one or more anomalies that include the first volume of the first medication delivered to the patient and/or the second volume of the second medication delivered to the patient being greater, less than, or equal to a threshold value. The tracking engine 110 may additionally and/or alternatively detect one or more anomalies that include a detected diversion event, such as when a discrepancy exists between an amount of medication delivered to the patient and an amount of medication that should remain to be delivered to the patient. The tracking engine 110 may generate an electronic alert that includes, for example, a wireless alert message such as, for example, a push notification, a short messaging service (SMS) message, and/or the like. The electronic alert may be sent to the client 130, which may be associated with a medical professional.

Figure 6:
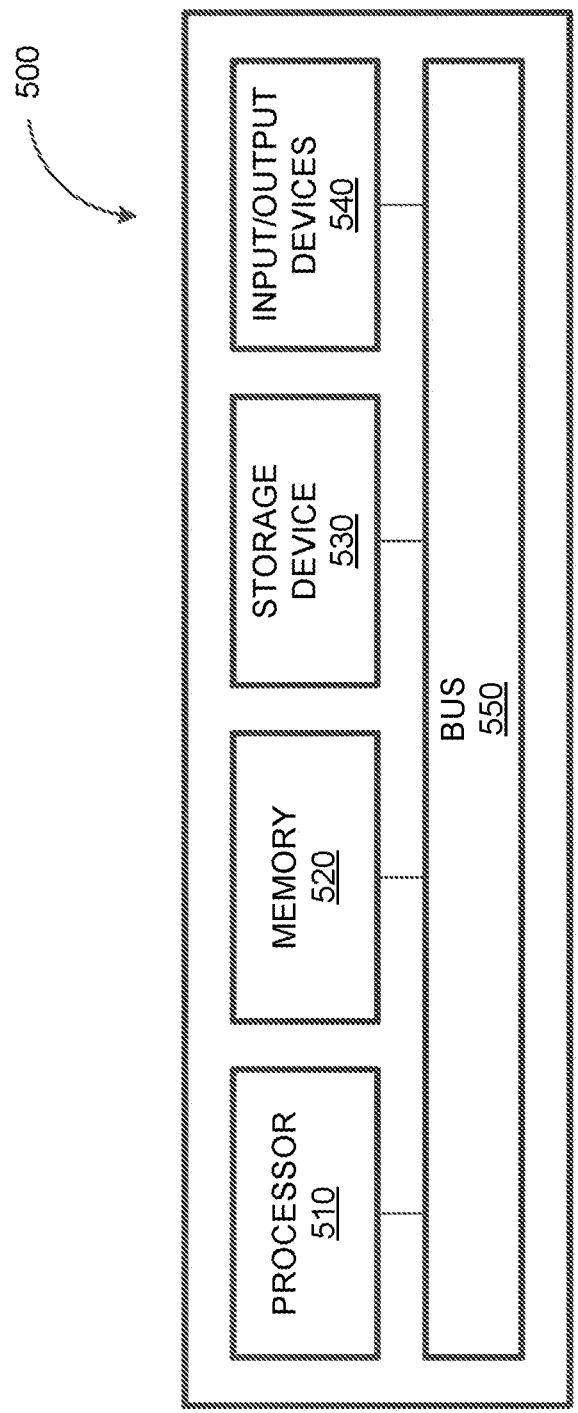
FIG. 6 depicts a block diagram illustrating a computing system, in accordance with some example embodiments.

FIG. 6 depicts a block diagram illustrating a computing system 500 consistent with implementations of the current subject matter. Referring to FIGS. 1 and 5, the computing system 500 can be used to implement the tracking engine 110 and/or any components therein.

As shown in FIG. 6, the computing system 500 can include a processor 510, a memory 520, a storage device 530, and input/output devices 540. The processor 510, the memory 520, the storage device 530, and the input/output devices 540 can be interconnected via a system bus 550. The processor 510 is capable of processing instructions for execution within the computing system 500. Such executed instructions can implement one or more components of, for example, the tracking engine 110. In some example embodiments, the processor 510 can be a single-threaded processor. Alternatively, the processor 510 can be a multi-threaded processor. The processor 510 is capable of processing instructions stored in the memory 520 and/or on the storage device 530 to display graphical information for a user interface provided via the input/output device 540.

As used herein a "user interface" (also referred to as an interactive user interface, a graphical user interface or a UI) may refer to a network based interface including data fields and/or other control elements for receiving input signals or providing electronic information and/or for providing information to the user in response to any received input signals. Control elements may include dials, buttons, icons, selectable areas, or other perceivable indicia presented via the UI that, when interacted with (e.g., clicked, touched, selected, etc.), initiates an exchange of data for the device presenting the UI. A UI may be implemented in whole or in part using technologies such as hyper-text mark-up language (HTML), FLASH™, JAVA™ .NET™, web services, or rich site summary (RSS). In some implementations, a UI may be included in a stand-alone client (for example, thick client, fat client) configured to communicate (e.g., send or receive data) in accordance with one or more of the aspects described. The communication may be to or from a medical device, diagnostic device, monitoring device, or server in communication therewith.

The memory 520 is a computer readable medium such as volatile or non-volatile that stores information within the computing system 500. The memory 520 can store data structures representing configuration object databases, for example. The storage device 530 is capable of providing persistent storage for the computing system 500. The storage device 530 can be a floppy disk device, a hard disk device, an optical disk device, or a tape device, or other suitable persistent storage means. The input/output device 540 provides input/output operations for the computing system 500. In some example embodiments, the input/output device 540 includes a keyboard and/or pointing device. In various implementations, the input/output device 540 includes a display unit for displaying graphical user interfaces.

According to some example embodiments, the input/output device 540 can provide input/output operations for a network device. For example, the input/output device 540 can include Ethernet ports or other networking ports to communicate with one or more wired and/or wireless networks (e.g., a local area network (LAN), a wide area network (WAN), the Internet).

In some example embodiments, the computing system 500 can be used to execute various interactive computer software applications that can be used for organization, analysis and/or storage of data in various formats. Alternatively, the computing system 500 can be used to execute software applications. These applications can be used to perform various functionalities, e.g., planning functionalities (e.g., generating, managing, editing of spreadsheet documents, word processing documents, and/or any other objects, etc.), computing functionalities, communications functionalities, etc. The applications can include various add-in functionalities or can be standalone computing products and/or functionalities. Upon activation within the applications, the functionalities can be used to generate the user interface provided via the input/output device 540. The user interface can be generated and presented to a user by the computing system 500 (e.g., on a computer screen monitor, etc.).

Figure 7A:
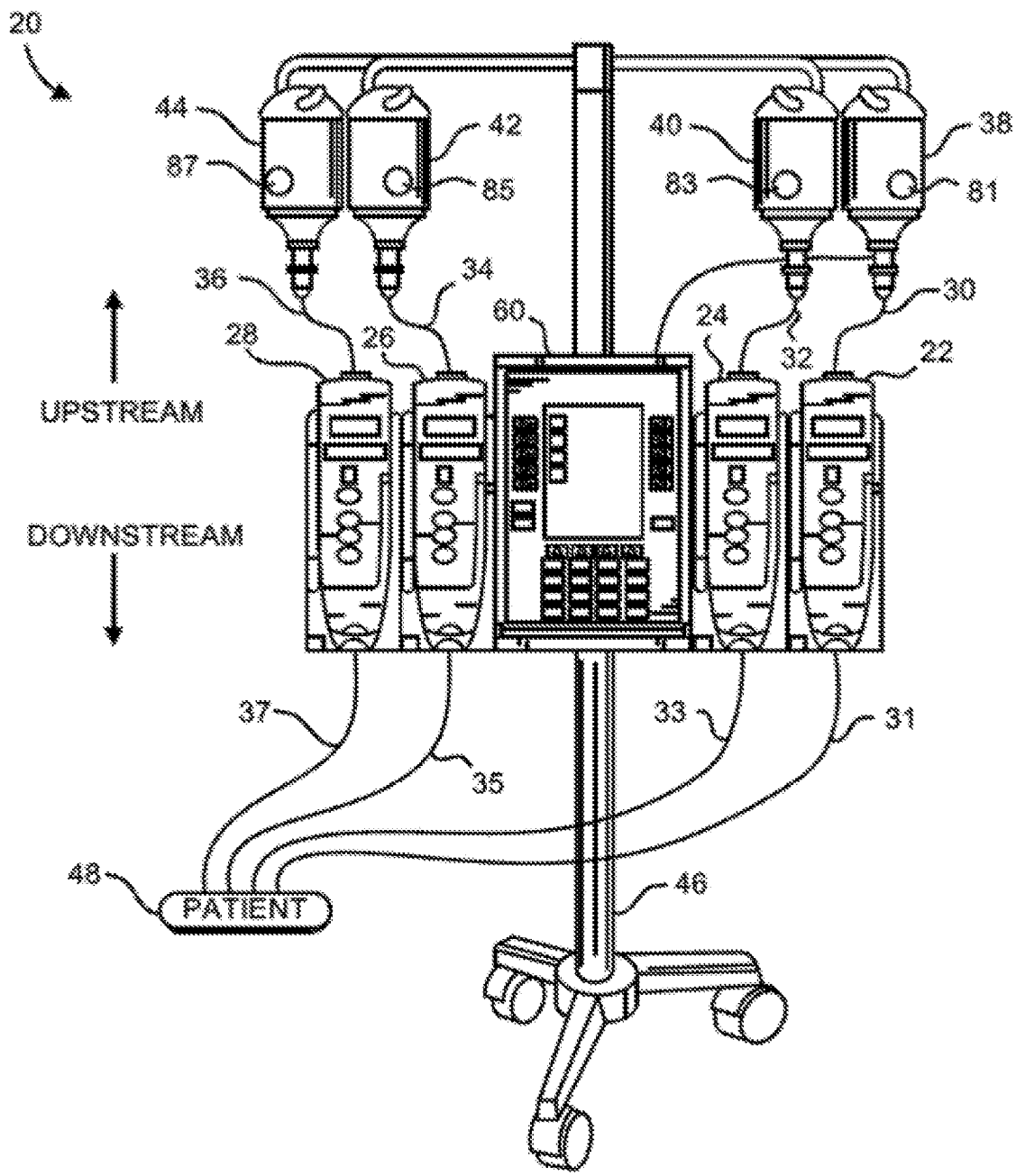
FIG. 7A depicts a front view of a patient care system, in accordance with some example embodiments.

In some example embodiments, the pump 22 may be part of a patient care system 20 shown in FIG. 7A. Referring to FIG. 7A, the patient care system 20 may include the pump 22 as well as additional pumps 24, 26, and 28. As shown in FIG. 7A, each of the pump 22, 24, 26, and 28 may be fluidly connected with an upstream fluid line 30, 32, 34, and 36, respectively. Moreover, each of the four pumps 22, 24, 26, and 28 may also fluidly connected with a downstream fluid line 31, 33, 35, and 37, respectively. The fluid lines can be any type of fluid conduit, such as tubing, through which fluid can flow. At least a portion of one or more of the fluid lines may be constructed with a multi-layered configuration as described herein.

Fluid supplies 38, 40, 42, and 44, which may take various forms but in this case are shown as bottles, are inverted and suspended above the pumps. Fluid supplies may also take the form of bags, syringes, or other types of containers. Both the patient care system 20 and the fluid supplies 38, 40, 42, and 44 are mounted to a roller stand or intravenous (IV) pole 46.

A separate pump 22, 24, 26, and 28 may be used to infuse each of the fluids of the fluid supplies into the patient. The pumps 22, 24, 26, and 28 may be flow control devices that will act on the respective fluid line to move the fluid from the fluid supply through the fluid line to the patient 48. Because individual pumps are used, each can be individually set to the pumping or operating parameters required for infusing the particular medical fluid from the respective fluid supply into the patient at the particular rate prescribed for that fluid by the physician. Such medical fluids may comprise drugs or nutrients or other fluids.

Typically, medical fluid administration sets have more parts than are shown in FIG. 7A. Many have check valves, drip chambers, valved ports, connectors, and other devices well known to those skilled in the art. These other devices have not been included in the drawings so as to preserve clarity of illustration. In addition, it should be noted that the drawing of FIG. 7A is not to scale and that distances have been compressed for the purpose of clarity. In an actual setting, the distance between the bottles 38, 40, 42, and 44 and the pump modules 22, 24, 26, and 28 could be much greater.

Figure 7B:
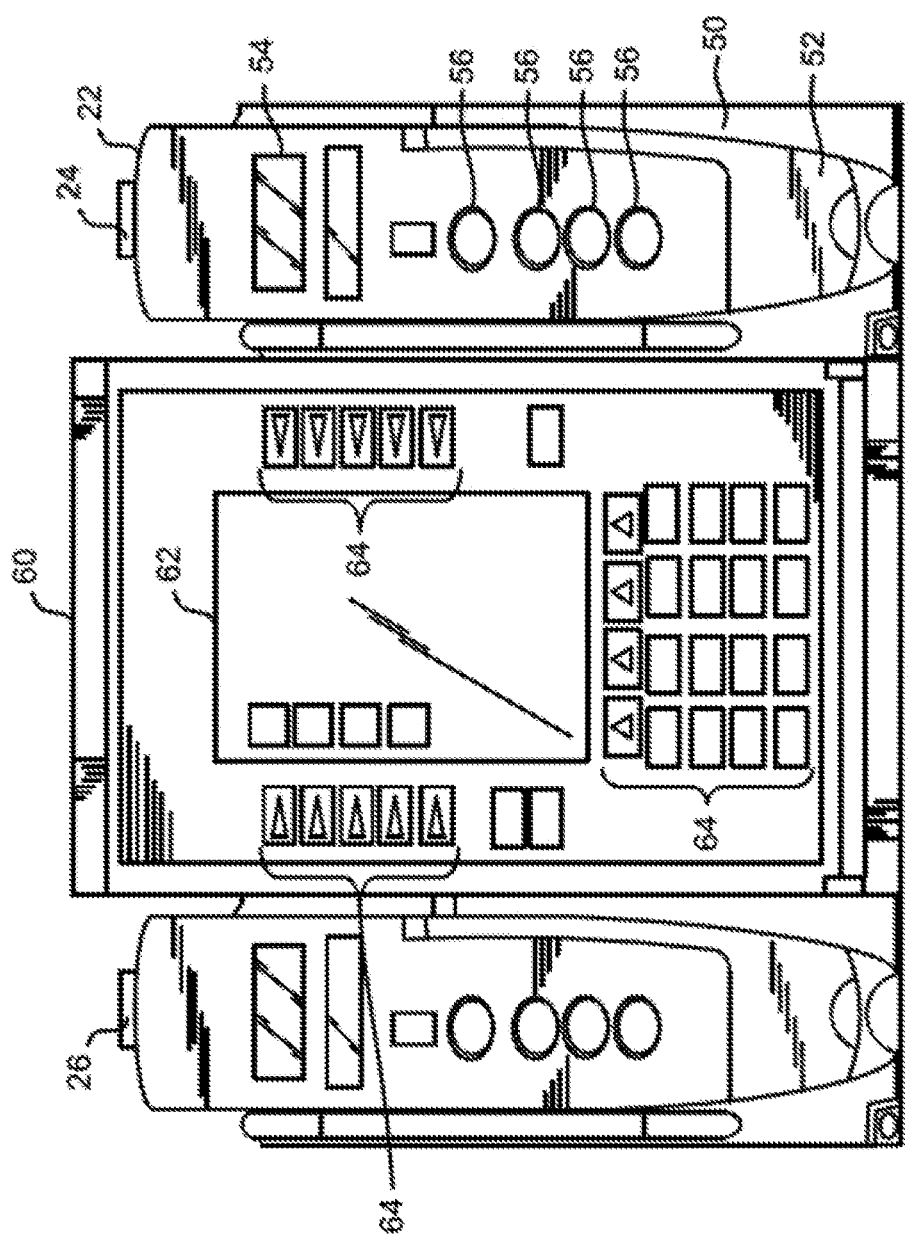
FIG. 7B depicts an enlarged view of a portion of a patient care system, in accordance with some example embodiments.

Referring now to FIG. 7B, an enlarged view of the front of the patient care system 20 is shown. The pump 22 may include a front door 50 and a handle 52 that operates to lock the door in a closed position for operation and to unlock and open the door for access to the internal pumping and sensing mechanisms and to load administration sets for the pump. When the door is open, the tube can be connected with the pump, as will be shown in FIG. 7C. When the door is closed, the tube is brought into operating engagement with the pumping mechanism, the upstream and downstream pressure sensors, and the other equipment of the pump. A display 54, such as an LED display, is located in plain view on the door in this embodiment and may be used to visually communicate various information relevant to the pump, such as alert indications (e.g., alarm messages). Control keys 56 exist for programming and controlling operations of the pump as desired. The pump 22 also includes audio alarm equipment in the form of a speaker (not shown).

In the embodiment shown, a programming module 60 is attached to the left side of the pump 22. Other devices or modules, including another pump, may be attached to the right side of the pump 22, as shown in FIG. 7A. In such a system, each attached pump represents a pump channel of the overall patient care system 20. In one embodiment, the programming module is used to provide an interface between the pump 22 and external devices as well as to provide most of the operator interface for the pump 22.

The programming module 60 includes a display 62 (which may include the user interface 300) for visually communicating various information, such as the operating parameters of the pump 22 and alert indications and alarm messages. The programming module 60 may also include a speaker to provide audible alarms. The programming module or any other module also has various input devices in this embodiment, including control keys 64 and a bar code or other scanner or reader for scanning information from an electronic data tag relating to the infusion, the patient, the care giver, or other. The programming module also has a communications system (not shown) with which it may communicate with external equipment such as a medical facility server or other computer and with a portable processor, such as a handheld portable digital assistant ("PDA), or a laptop-type of computer, or other information device that a care giver may have to transfer information as well as to download drug libraries to a programming module or pump. In some implementations, the pump 22 may provide volume data to the programming module 60, which, in turn, may maintain the counters and/or cause transmission of alert messages associated with detected anomalies. In such implementations, the programming module 60 may communicate with the tracking engine 110, include the tracking engine 110, or implement features of the tracking engine 110 described herein.

The communications system may take the form of a radio frequency ("RF") (radio frequency) system, an optical system such as infrared, a Blue Tooth system, or other wired or wireless system. The bar code scanner and communications system may alternatively be included integrally with the pump 22, such as in cases where a programming module is not used, or in addition to one with the programming module. Further, information input devices need not be hard-wired to medical instruments, information may be transferred through a wireless connection as well.

FIG. 7B includes a second pump 26 connected to the programming module 60. As shown in FIG. 7A, more pump modules may be connected. Additionally, other types of modules may be connected to the pump modules or to the programming module. In such implementations, the tracking engine 110 may maintain respective dose type counters for each pump (e.g., pump 22 and pump 26).

Figure 7C:
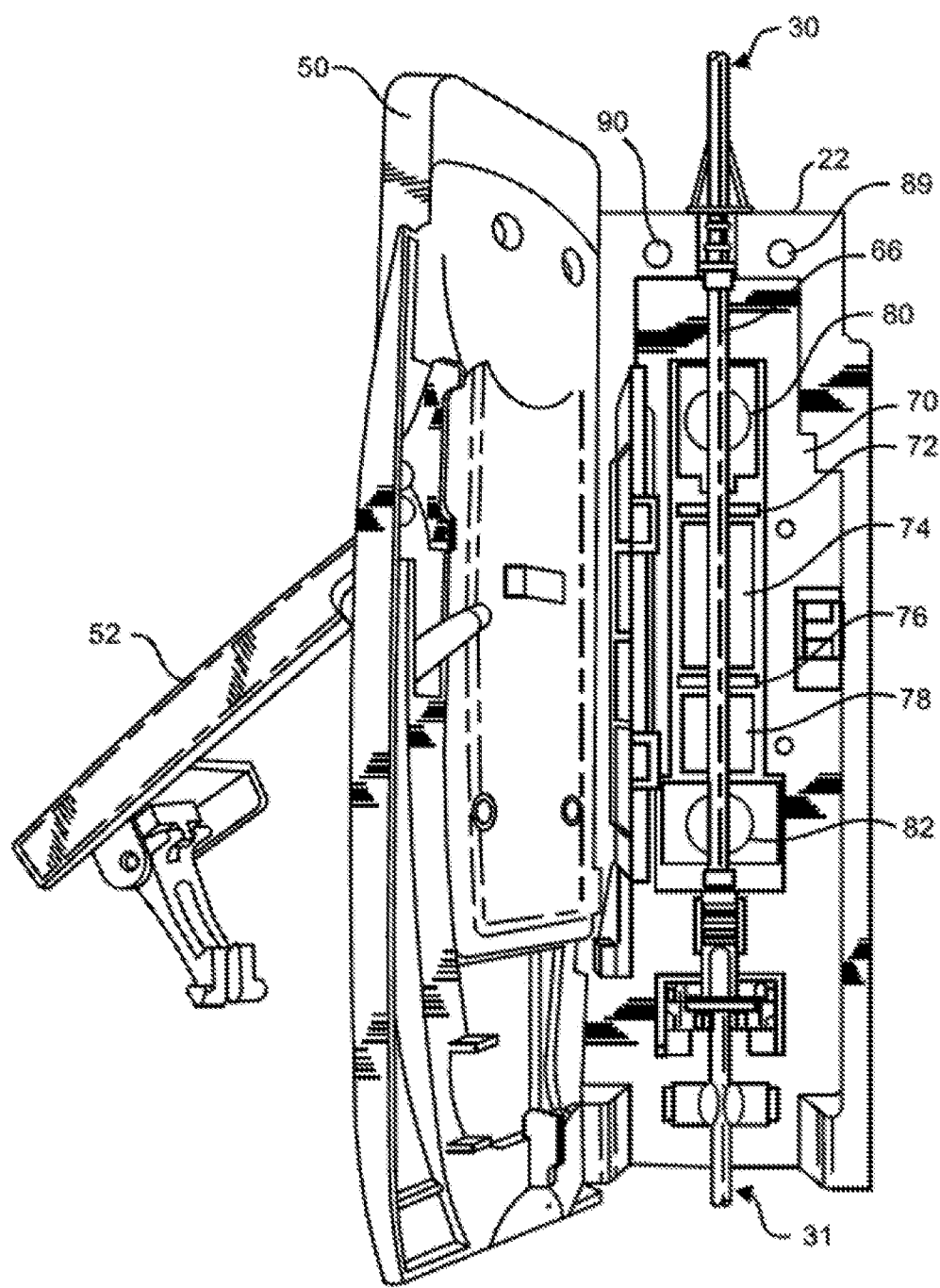
FIG. 7C depicts a perspective view of a pump, in accordance with some example embodiments.

Turning now to FIG. 7C, the pump 22 is shown in perspective view with the front door 50 open, showing the upstream fluid line 30 and downstream fluid line 31 in operative engagement with the pump 22. The pump 22 directly acts on a tube 66 (also referred to as a pump segment) that connects the upstream fluid line 30 to the downstream fluid line 31 to form a continuous fluid conduit, extending from the respective fluid supply 38 (FIG. 7A) to the patient 48, through which fluid is acted upon by the pump to move fluid downstream to the patient. Specifically, a pumping mechanism 70 acts as the flow control device of the pump to move fluid though the conduit. The upstream and downstream fluid lines and/or tube 66 may be coupled to a pump cassette or cartridge that is configured to be coupled to the pump 22, such as the type described in co-pending U.S. patent application Ser. No. 13/827,775, which is incorporated by reference herein.

The type of pumping mechanism may vary and may be for example, a multiple finger pumping mechanism. For example, the pumping mechanism may be of the "four finger" type and includes an upstream occluding finger 72, a primary pumping finger 74, a downstream occluding finger 76, and a secondary pumping finger 78. The "four finger" pumping mechanism and mechanisms used in other linear peristaltic pumps operate by sequentially pressing on a segment of the fluid conduit by means of the cam-following pumping fingers and valve fingers 72, 74, 76, and 78. The pressure is applied in sequential locations of the conduit, beginning at the upstream end of the pumping mechanism and working toward the downstream end. At least one finger is always pressing hard enough to occlude the conduit. As a practical matter, one finger does not retract from occluding the tubing until the next one in sequence has already occluded the tubing; thus at no time is there a direct fluid path from the fluid supply to the patient. The operation of peristaltic pumps including four finger pumps is well known to those skilled in the art and no further operational details are provided here.

In this particular embodiment, FIG. 7C further shows a downstream pressure sensor 82 included in the pump 22 at a downstream location with respect to the pumping mechanism. The downstream pressure sensor 82 is mounted to the flow control device 70 and is located adjacent and downstream in relation to the flow control device. The downstream pressure sensor is located downstream from the flow control device, that is, at a location between the patient 48 (FIG. 7A) and the flow control device, so that the connection of the correct fluid supply with the correct pump may be verified before any fluid is pumped to the patient.

With reference still to FIG. 7C, an upstream pressure sensor 80 may also be included in the pump 22. The upstream pressure sensor is assigned to the flow control device or pumping mechanism 70 and, in this embodiment, is further provided as an integral part of the pump 22. It is mounted to the flow control device 70 and is located adjacent and upstream in relation to the flow control device. The upstream pressure sensor is located upstream from the flow control device, that is, at a location between the fluid supply 38 (FIG. 7A) and the flow control device, so that the connection of the correct fluid supply with the correct pump may be verified before any fluid is pumped to the patient. In an implementation where the source is a syringe, the flow control device 70 may be configured to press a plunger of the syringe to provide the infusion according to the programmed parameters.

One or more aspects or features of the subject matter described herein can be realized in digital electronic circuitry, integrated circuitry, specially designed ASICs, field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example, as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including acoustic, speech, or tactile input. Other possible input devices include touch screens or other touch-sensitive devices such as single or multi-point resistive or capacitive track pads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

As used herein, the terms "determine" or "determining" encompass a wide variety of actions. For example, "determining" may include calculating, computing, processing, deriving, generating, obtaining, looking up (e.g., looking up in a table, a database or another data structure), ascertaining and the like via a hardware element without user intervention. Also, "determining" may include receiving (e.g., receiving information), accessing (e.g., accessing data in a memory) and the like via a hardware element without user intervention. "Determining" may include resolving, selecting, choosing, establishing, and the like via a hardware element without user intervention.

As used herein, the terms "provide" or "providing" encompass a wide variety of actions. For example, "providing" may include storing a value in a location of a storage device for subsequent retrieval, transmitting a value directly to the recipient via at least one wired or wireless communication medium, transmitting or storing a reference to a value, and the like. "Providing" may also include encoding, decoding, encrypting, decrypting, validating, verifying, and the like via a hardware element.

As used herein, the term "message" encompasses a wide variety of formats for communicating (e.g., transmitting or receiving) information. A message may include a machine readable aggregation of information such as an XML document, fixed field message, comma separated message, or the like. A message may, in some implementations, include a signal utilized to transmit one or more representations of the information. While recited in the singular, it will be understood that a message may be composed, transmitted, stored, received, etc. in multiple parts.

As user herein, the terms "correspond" or "corresponding" encompasses a structural, functional, quantitative and/or qualitative correlation or relationship between two or more objects, data sets, information and/or the like, preferably where the correspondence or relationship may be used to translate one or more of the two or more objects, data sets, information and/or the like so to appear to be the same or equal. Correspondence may be assessed using one or more of a threshold, a value range, fuzzy logic, pattern matching, a machine learning assessment model, or combinations thereof.

In some embodiments, data can be forwarded to a "remote" device or location," where "remote," means a location or device other than the location or device at which the program is executed. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet or including email transmissions and information recorded on websites and the like.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A system, comprising:
   at least one data processor; and
   at least one memory storing instructions which, when executed by the at least one data processor, result in operations comprising:
      receiving, from a volume meter at a pump, a first data indicative of a volume of a first fluid present in a first fluid container inserted in the pump, the pump being configured to deliver the first fluid to a patient;
      updating, based at least on the first data, a first counter in response to the first fluid being delivered to the patient from the first fluid container as a first fluid type or a second counter in response to the first fluid being delivered to the patient from the first fluid container as a second fluid type;
      determining, based at least on at least one of the first counter and the second counter, a first volume of the first fluid delivered to the patient; and
      receiving, from a device communicatively coupled with the pump, an updated treatment plan in response to one or more anomalies being present in the first volume of the first fluid delivered to the patient.

2. The system of claim 1, wherein the first volume comprises at least one of a first individual volume of the first fluid that is delivered to the patient as the first fluid type, a second individual volume of the first fluid that is delivered to the patient as the second fluid type, and a total volume of the first fluid that is delivered to the patient as the first fluid type and the second fluid type.

3. The system of claim 1, wherein the operations further comprise:
   receiving, from a tag reader at the pump, a second data identifying a second fluid in a second fluid container that is inserted into the pump to replace the first fluid container; and
   in response to the second fluid being a different fluid than the first fluid included in the first fluid container, resetting the first counter and the second counter.

4. The system of claim 3, wherein the operations further comprise:
   updating the first counter in response to the second fluid being delivered to the patient as at least one of the first fluid type an the second counter in response to the second fluid being delivered to the patient as the second fluid type.

5. The system of claim 3, wherein the operations further comprise:
in response to the second fluid being a same fluid as the first fluid,
updating at least one of the first counter in response to the first fluid being delivered to the patient from the second fluid container as the first fluid type and the second counter in response to the first fluid being delivered to the patient from the second fluid container as the second fluid type.

6. The system of claim 3, wherein the operations further comprise:
in response to the second data indicating that the second fluid container is associated with a different patient than the first fluid container, resetting the first counter and the second counter.

7. The system of claim 3, wherein the tag reader is configured to read at least one of a first identifier tag associated with the first fluid container and a second identifier tag associated with the second fluid container, and wherein at least one of the first identifier tag and the second identifier tag comprise at least one of a barcode, a quick response (QR) code, and a radio frequency identification (RFID) tag.

8. The system of claim 1, wherein the first fluid type and the second fluid type comprises a different one of a patient demand dose, a clinician dose, a loading dose, and a maintenance dose.

9. The system of claim 1, wherein the one or more anomalies include the first volume being greater than a maximum threshold value or less than a minimum threshold value.

10. The system of claim 1, wherein the operations further comprise: sending, to the device, an electronic alert in response to the one or more anomalies being present in the first volume of the first fluid delivered to the patient, the electronic alert comprising at least one of a push notification and a short messaging service (SMS) message.

11. A computer-implemented method, comprising:
receiving, from a volume meter at a pump, a first data indicative of a volume of a first fluid present in a first fluid container inserted in the pump, the pump being configured to deliver the first fluid to a patient;
updating, based at least on the first data, a first counter in response to the first fluid being delivered to the patient from the first fluid container as a first fluid type or a second counter in response to the first fluid being delivered to the patient from the first fluid container as a second fluid type;
determining, based at least on at least one of the first counter and the second counter, a first volume of the first fluid delivered to the patient; and
receiving, from a device communicatively coupled with the pump, an updated treatment plan in response to one or more anomalies being present in the first volume of the first fluid delivered to the patient.

12. The method of claim 11, wherein the first volume comprises at least one of a first individual volume of the first fluid that is delivered to the patient as the first fluid type, a second individual volume of the first fluid that is delivered to the patient as the second fluid type, and a total volume of the first fluid that is delivered to the patient as the first fluid type and the second fluid type.

13. The method of claim 11, further comprising:
receiving, from a tag reader at the pump, a second data identifying a second fluid in a second fluid container that is inserted into the pump to replace the first fluid container; and
in response to the second fluid being a different fluid than the first fluid included in the first fluid container, resetting the first counter and the second counter.

14. The method of claim 13, further comprising:
updating at least one of the first counter in response to the second fluid being delivered to the patient as the first fluid type and the second counter in response to the second fluid being delivered to the patient as the second fluid type.

15. The method of claim 13, further comprising:
in response to the second fluid being a same fluid as the first fluid,
updating at least one of the first counter in response to the first fluid being delivered to the patient from the second fluid container as the first fluid type and the second counter in response to the first fluid being delivered to the patient from the second fluid container as the second fluid type.

16. The method of claim 13, further comprising:
in response to the second data indicating that the second fluid container is associated with a different patient than the first fluid container, resetting the first counter and the second counter.

17. The method of claim 13, wherein the tag reader is configured to read at least one of a first identifier tag associated with the first fluid container and a second identifier tag associated with the second fluid container, and wherein at least one of the first identifier tag and the second identifier tag comprise at least one of a barcode, a quick response (QR) code, and a radio frequency identification (RFID) tag.

18. The method of claim 11, wherein the first fluid type and the second fluid type comprises a different one of a patient demand dose, a clinician dose, a loading dose, and a maintenance dose.

19. The method of claim 11, wherein the one or more anomalies include the first volume being greater than a maximum threshold value or less than a minimum threshold value.

20. A non-transitory computer-readable storage medium including program code, which when executed by at least one data processor, cause operations comprising:
receiving, from a volumetric device communicatively coupled with a pump, a first data indicative of a volume of a first fluid present in a first fluid container inserted in the pump, the pump being configured to deliver the first fluid to a patient;
updating, based at least on the first data, a first counter in response to the first fluid being delivered to the patient from the first fluid container as a first fluid type or a second counter in response to the first fluid being delivered to the patient from the first fluid container as a second fluid type;
determining, based at least on at least one of the first counter and the second counter, a first volume of the first fluid delivered to the patient; and
receiving, from a device communicatively coupled with the pump, an updated treatment plan in response to one or more anomalies being present in the first volume of the first fluid delivered to the patient.

* * * * *